United States Patent [19]

Chapman

[11] Patent Number: 5,663,045
[45] Date of Patent: Sep. 2, 1997

[54] METHOD FOR TESTING BLOOD UNITS FOR VIRAL CONTAMINATION

[75] Inventor: John R. Chapman, Lake Villa, Ill.

[73] Assignee: Baxter International Inc., Deerfield, Ill.

[21] Appl. No.: 456,443

[22] Filed: Jun. 1, 1995

Related U.S. Application Data

[63] Continuation of Ser. No. 37,525, Mar. 24, 1993, Pat. No. 5,498,520.

[51] Int. Cl.$^6$ ............................ C12Q 1/70; C12Q 1/68; B01D 33/15; B01D 21/26
[52] U.S. Cl. ........................ 435/5; 435/6; 435/7.1; 435/91.2; 435/2; 210/789; 210/782; 424/93.72; 424/93.74
[58] Field of Search .................... 435/5, 6, 2, 7.1, 435/91.2; 210/789, 782; 436/177, 178; 424/93.72, 93.74

[56] References Cited

U.S. PATENT DOCUMENTS 5,298,165  3/1994  Oka et al. ........................ 210/645

OTHER PUBLICATIONS

Simmonds et al. (Feb. 1990) J. Virology 64(2):864–872.
Keller et al, *DNA PROBES*, Macmillan Publishers Ltd. (U.K.), pp. 36–39; 385–386; 389–403 (1993).
Barbara et al, *Polymerase Chain Reaction and Transfusion Microbiology* Vox Sang. vol. 64, pp. 73–81 (1993).
Hogman et al, *The Bottom and Top System: A New Technique for Blood Component Preparation and Storage*, Vox Sang, vol. 55, pp. 211–217 (1988).
Frewin et al, *A Comparative Study of the Effect of Three Methods of Leukocyte Removal on Plasma Histamine Levels in Stored Human Blood*, Seminars in Hematology, vol. 28, No. 3, pp. 18–21 (1991).
Barre-Sinoussi et al, *Isolation of a T–Lymphotropic Retrovirus from a Patient at Risk for Acquired Immune Deficiency Syndrome (AIDS)*, Science, vol. 220, pp. 868–871 (1983).
Perrow, *The Preparation of Leucocyte Homogenates for Enzymatic Assays*, New Zealand Journal of Laboratory Techniques, vol. 31, No. 1, pp. 6–9 (1977).
Bruisten et al, *Efficiency of White Cell Filtration and a Freeze–Thaw Procedure for Removal of HIV–infected Cells from Blood*, Transfusions, vol. 30, No. 9, pp. 833–837 (1990).

*Primary Examiner*—Lisa B. Arthur
*Attorney, Agent, or Firm*—Robert M. Barrett; Denise M. Serewicz; Bradford R. L. Price

[57] ABSTRACT

The present invention provides a method for testing a blood unit for viral contamination without rendering the blood unit unusable for therapeutic applications. The method comprises the steps of: removing and collecting from a blood unit a majority of the leukocytes present therein; and using the collected leukocytes to test the blood unit for viral contamination. The present invention also provides a method for validating viral inactivation processes.

5 Claims, 3 Drawing Sheets

METHOD FOR TESTING BLOOD UNITS FOR VIRAL CONTAMINATION

This is a continuation of application Ser. No. 08/037,525, filed on Mar. 24, 1993, now U.S. Pat. No. 5,498,520, issued Mar. 12, 1996.

BACKGROUND OF THE INVENTION

The present invention relates generally to diagnostic techniques. More specifically, the present invention relates to the testing of blood units for viral contamination.

In a variety of therapies, such as transfusion and transplants, body fluids, especially blood components, such as red blood cells, platelets, plasma, and bone marrow, are infused from one or more individuals into a patient. Although such therapies provide treatments, some of which are life saving, that cannot otherwise be provided, due to the transmission of infectious diseases there may be potential risks to such therapies.

For example, it is known that blood can carry infectious agents, such as hepatitis virus, human immunodeficiency virus (an etiological agent for AIDS), cytomegalovirus, Epstein Barr virus, and herpes virus. Although screening methods exist to identify blood that may include such viruses, current screening methods do not assure that every blood unit that contains such a virus is identified.

In this regard, one of the difficulties in testing blood components for viral contamination, such as HIV, is that many current diagnostic tests are based on an identification of antibodies. Accordingly, they will only exhibit a positive test result if the blood unit includes antibodies for the virus, e.g., anti-HIV. With respect to intracellular viral infections, an individual, however, does not generate antibodies immediately upon infection. Rather there is a "window period" that extends from the initial infection of the patient with a virus to the generation of antibodies. When an individual is in this window period, diagnostic tests that are based on antibodies will not identify the individual, or the blood unit, as being infected. But, even though antibodies are not present, the blood unit can still transmit an infection.

It is believed that this window period, with respect to HIV infection, extends from approximately six weeks to 48 months. During this time period, an individual who has been infected with HIV and accordingly, whose blood will transmit same, will register a negative antibody response. Therefore, current screening methods will not identify as viral contaminated a blood unit from an individual who is infected with HIV but who has not generated anti-HIV.

In order to identify blood units that may be contaminated because an individual is within the window period, recent attempts have focussed on the use of nucleic acid sequencing diagnostic techniques. Specifically, attempts have been made to use polymerase chain reaction (PCR) techniques for detecting nucleotide sequences for HIV virus.

A number of methods of using PCR are known. Briefly, in one PCR method, a sample containing DNA is placed in a reaction tube including appropriate buffers, nucleoside triphosphates, a thermostable DNA polymerase and oligonucleotide primers complementary to the ends of a region of DNA of interest. Initially, to denature the double-stranded DNA under study, the temperature of the reaction is rapidly increased. The temperature is then decreased allowing the oligonucleotide primers to anneal to their complementary sequences. By increasing the temperature, a DNA extension occurs at the optimal temperature of activity for the polymerase. By repeating these cycles of denaturation annealing-extension, a single sequence of a few hundred base pairs can be amplified. This amplification can be in the range of a factor of $10^6$ and detected with relative ease. Conway, "Detection of HIV-1 by PCR in Clinical Specimens", "Techniques in HIV Research", Stockton Press (1990).

Although nucleic acid sequencing techniques are very sensitive, they are also sample specific. Moreover, the samples of the blood units so tested are rendered unusable for therapeutic applications. Because of this, currently nucleic acid sequencing diagnostic methods do not provide a method for insuring that blood units do not have viral contamination.

For example, if one were to attempt to use a PCR technique to test a sample of a blood unit using standard technology, one could not insure that the unit did not contain viral contamination even if the test was negative. In this regard, because a PCR test is sample specific unless the whole blood unit was tested, it would not accurately reflect that the unit did not include viral contamination; if only a 10 ml sample were tested, the remaining 290 ml of a 300 ml could contain a viral contaminant.

A PCR test will only determine if there is a viral agent in the sample being assayed, not in the entire unit. Because the test destroys the viability of the component, heretofore, it was not possible to test the entire component to ensure that it is not contaminated with, for example, HIV.

Accordingly, there is a need for improved diagnostic testing of blood units to determine viral contamination during the "window period" of contamination.

SUMMARY OF THE INVENTION

The present invention provides a method for testing a blood unit for viral contamination that does not render the blood unit unusable for therapeutic applications. The method allows one to effectively sample the entire blood unit using, for example, nucleic acid sequencing techniques. The method improves the accuracy of diagnostic tests for viral contaminants.

Although typically to increase the accuracy of a diagnostic test for infectious disease it is desirable to increase the sample volume of the material being assayed, with respect to blood components this is not possible. In the case of blood and its components, only a small fraction of the total volume of the blood component can be sacrificed for performance of diagnostic assays for infectious diseases. The inability to sample the whole blood unit places a finite limit on the accuracy of diagnostic testing (including nucleic acid amplification technology) due to sampling volume. In this regard: 1) the assay result can be a true negative, but the unit positive; or 2) the assay result can be a false negative due to lack of sensitivity of the assay. The present invention addresses both of these limitations.

To this end, the present invention provides a method for testing a blood unit for viral contamination without rendering the blood unit unusable for therapeutic applications. The method comprises the steps of: removing and collecting from a blood unit a majority of the leukocytes present therein; and using the collected leukocytes to test the blood unit for viral contamination.

In an embodiment, the present invention provides a method for testing a blood unit for viral contamination without rendering the blood unit unusable for therapeutic applications comprising the steps of: passing a blood component through a leukocyte filter to remove a majority of the leukocytes contained within the blood component; collecting a resultant filtered blood component; creating a cell lysate by passing a lysing reagent through the leukocyte filter; and assaying the cell lysate for viral contaminants.

In an embodiment, the method includes the step of culturing the filter before passing a lysing reagent through the filter. The filter can be cultured for 1 to 5 days.

In an embodiment, the present invention provides a method for testing a blood unit for viral contamination without rendering the blood unit unusable for therapeutic applications comprising the steps of separating the blood unit into a plasma rich platelet component, a buffy layer, and a red blood cell component; removing the buffy layer; and assaying the buffy layer for viral contamination.

The present invention also provides a process that can be used in validation studies for viral inactivation or removal processes.

To this end, a method for the validation of a viral inactivation process is provided comprising the steps of: adding a virus to a blood component (or in the alternative, using a naturally contaminated blood component); treating the blood component with a viral inactivation process; adding virus host cells to the blood component; filtering the blood component to remove the virus host cells; and testing the virus host cells for viral contaminants.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an improved method for testing a blood component for a viral contaminant. The method of the present invention improves the accuracy of diagnostic tests without sacrificing the blood unit to be administered. To this end, the process of the present invention allows the entire unit of whole blood, red blood cells, or platelet concentrate to be sampled for viral contamination without rendering the cell product unusable for therapeutic applications.

In an embodiment, the invention includes the steps of using a filter to capture leukocytes without damaging the blood components.

There are three principal indications for the transfusion of a blood product: 1) deficiency in oxygen-carrying red blood cells; 2) deficiency in hematologic factors related to blood clotting, includes platelets or protein coagulation factors; and 3) deficiency in plasma volume. Patients requiring a transfusion do not receive whole blood but the specific component required to overcome the clinical deficiency. For example, patients undergoing chemotherapy or radiation therapy require primarily platelets and to a lesser degree red cells. Bone marrow or other organ transplant and dialysis patients generally require only red blood cells.

Leukocytes are unwanted because they are not relevant to the therapeutic effects of oxygen-carrying red blood cells, platelet or plasma, and have been implicated as increasing the risks associated with blood transfusion for their role in alloimmunization to HLA antigens and post transfusion infection by acting as virus carrying cells. Typically, the leukocytes are removed by a filtering process in approximately 10% of the blood components that are transfused.

When a filtering process is used, the leukocytes captured in these filters are discarded. As set forth in detail below, pursuant to the present invention, the filters containing the leukocytes can be used as a starting material for a process to recover and/or amplify viral markers (viral nucleic acid sequences and/or antigens).

Pursuant to an embodiment of the present invention, a majority, greater than 50%, of the leukocytes are collected. Depending on the method used, up to 99.8% of the leukocytes may be collected. Leukocytes typically comprise 0.25% of the cellular composition of blood. A leukocyte count of 7.5 million/ml of blood is considered average for an adult. In a 500 ml unit of whole blood, containing 63 ml of anticoagulant solution, $3.2\times10^9$ leukocyte cells will be present.

Because the leukocytes are a source of infectivity in the blood, they provide a desirable material for diagnostic assays. Furthermore, because the collected leukocytes are derived from the entire unit of blood component to be transfused, as opposed to a small segment thereof, an improved diagnostic procedure is achieved.

Figure 1:
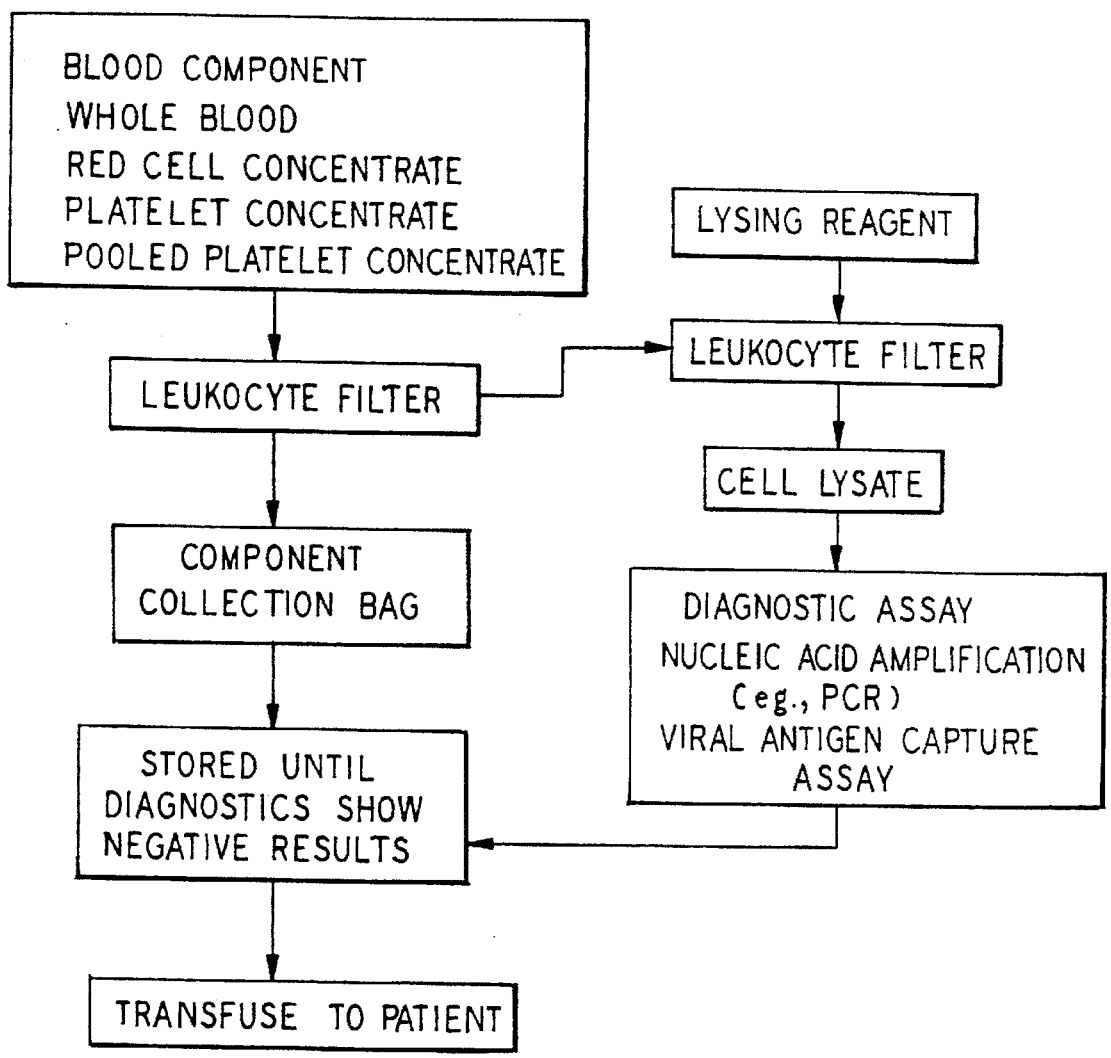
FIG. 1 illustrates schematically an embodiment of the method of the present invention for testing a blood component for viral contamination.

FIG. 1 illustrates schematically an embodiment of the process of the present invention. The blood component (which can be whole blood, red cell concentrate, platelet concentrate, or pooled platelet concentrate) is first passed through a filter which is designed to capture 90 to greater than 99% of the leukocytes present.

Leukocyte filters that can be used pursuant to the present invention include the Sepacell R-500 filter available from Asahi Corp., Tokyo, Japan and the RC-100 for blood filtration and PL-100 for platelet filtration, both available from Pall Biomedical Corp., East Hills, New York. It has been reported in Biotechnology & Medical, Aug. 19, 1988 that an Asahi filter is able to remove 99.8% of the leukocytes present in whole blood.

The filtered blood component is collected in a blood collection bag. The blood component is stored pending the results of the diagnostic test.

Pursuant to the present invention, the leukocyte filter is utilized as a source material for diagnostic tests for infectious disease antigen and nucleic acid sequences. To this end, the filter is treated to lyse the cells contained in the filter. This allows the recovery of nucleic acids and antigens that are contained on and within the leukocytes.

The cells are lyse by using a lysing reagent. The lysing reagent preferably will be a solution containing a detergent to break the cytoplasmic membrane and release the nuclei of the cells.

The cell lysate is then flushed out of the filter using an isotonic saline solution and collected. This resultant cell lysate is then used as a test material for diagnostic assays (nucleic acid amplification technology for viral nucleic acid sequences, e.g., PCR or 3SR or viral antigens, e.g., enzyme-linked immunoadsorbent assays).

Because the assay, pursuant to the present invention, will be based on an analysis of the great majority of the leukocytes present in the blood unit, even when using sample specific analysis such as PCR methods one can be assured that a negative result is accurate even if an individual is in a window period of infection.

Once a negative result is obtained using the cell lysate, the blood component contained in the collection container can then be transfused into a patient.

Figure 2:
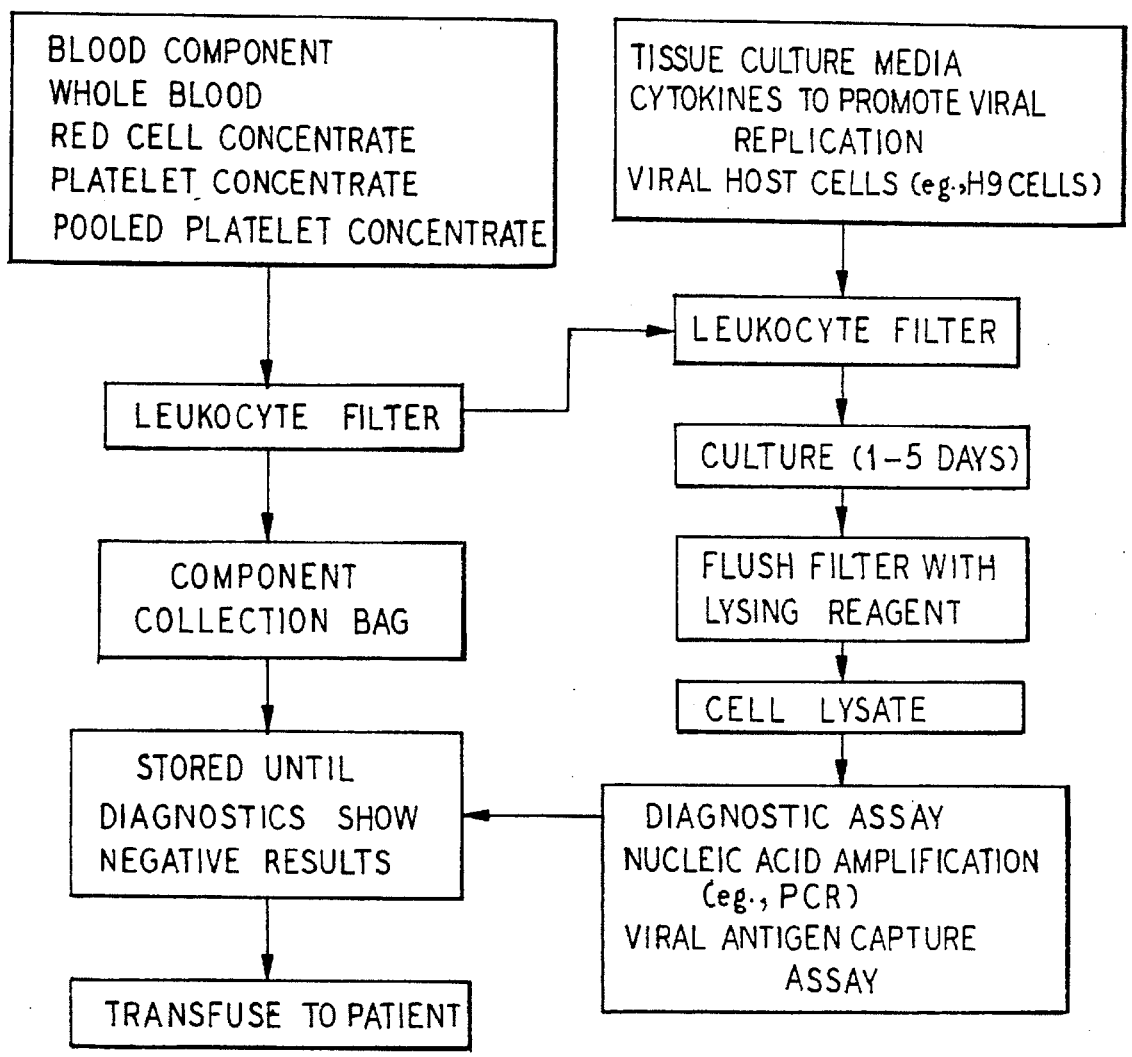
FIG. 2 illustrates schematically a further embodiment of the method of the present invention for testing a blood component for vital contamination.

FIG. 2 illustrates schematically another embodiment of the present invention. If necessary to increase assay sensitivity (particularly for antigen capture assay systems), the leukocyte filter can be utilized as a culture chamber for viral replication.

In this case, again a blood component (whole blood, red cell concentrate, platelet concentrate, or pooled platelet concentrate) is filtered through a leukofilter. The leukofilter is separated from the blood bag container, containing the filtered blood component, and the filter is flushed with tissue culture media such as 10% Fetal Calf Serum in RPMI 1640 media. In some cases, it may be desirable to supplement the media with cytokines (e.g., IL-2 or T-cell mitogen (e.g., PHA)) to promote viral replication in the leukocytes and to sustain the viability of the cells in the filter.

In addition, in some cases, it may be desirable if the tissue culture media is supplemented with viral host cell lines (example H9 cells for HIV). In this case, the filter would be used as a culture chamber for the leukocytes captured from the blood and for virus host cells. The H9 cells can then be infected by HIV present in the captured leukocytes and can serve to amplify the production of viral antigen (e.g., HIV p24 antigen).

After the appropriate culture period of approximately 1 to 5 days, the filter can be treated to accomplish lysis of the trapped cells by one of several means (freeze-thaw, detergent, hypotonic shock). The resulting cell lysate can then be collected by flushing the filter with an isotonic saline solution.

The collected cell lysate can be tested using conventional antigen capture assay systems such as, for example, DuPont HIV p24 Care Profile, Elisa Kit or Coulter HIV p24 Antigen Assay (Hialeah, Fla.) for the HIV p24 antigen or by nucleic acid amplification methodologies, such as Gene Amplimer HIV-1 Reagents with GeneAmp® PCR Core Reagents and Perkin-Elmer Cetus DNA Thermal Cycler, available from Perkin-Elmer Cetus. In some cases, the cell lysis may not be required due to release of the virus into the tissue culture media from infected cells.

Again, by using this method, even if a sample specific diagnostic test is used, because the test is with respect to the great majority of leukocytes present, a negative test will ensure that the blood component is not contaminated. The blood component contained in the blood bag container can then be transfused into a patient.

In an embodiment of the method of the present invention, instead of filtering the blood component to capture the leukocytes, centrifugation processes that separate a whole blood unit into various components can be used. During a typical centrifugation process, the whole blood is separated in a top portion including platelet rich plasma, a middle or buffy coat layer containing white cells and leukocytes, and a bottom red blood cell rich layer. Typically, the buffy coat layer is discarded.

Pursuant to the present invention, the buffy coat layer is used for diagnostic applications. To this end, the buffy coat can be subjected to nucleic acid amplification, e.g., PCR or 3SR or viral antigen capture assay. By testing the buffy coat layer, if a negative test results, one is assured that both the platelet rich plasma component and red blood cell component are viral contaminant free. It is believed that by collecting the buffy coat using standard techniques, at least approximately 80% of the leukocytes are recovered.

In an embodiment, the following method is used:
1. Centrifuge the blood bag in an inverted position in a refrigerated centrifuge containing whole blood at 5° C. using a "heavy" spin.
2. Hang the centrifuged, inverted bag on a ring stand or inverted plasma expressor. The temperature of the blood must not exceed 10° C. during the procedure. Allow the bag to hang undisturbed for Several minutes.
3. Place the transfer bag on a scale (e.g., dietary scale) below the blood bag. Adjust the scale to zero.
4. Penetrate the closure of the primary bag, avoiding agitation of the contents and allow red blood cells to flow to the transfer bag. At least 80% of the red blood cells must be transferred to the satellite bag. To calculate the amount of red blood cells to be expressed estimate the amount of blood (excluding anticoagulant) in the bag multiplied by the donor's hematocrit (assume 40% for females and 43% for males) (1 ml of red blood cells (RBC) weighs 1.06 gm).
5. The remaining blood in the bag contains the buffy coat, some residual red blood cells, and the plasma.
6. The contents are mixed and the preparation is centrifuged to pellet the buffy coat.
7. The plasma is expressed into a satellite container.
8. The residual red cells in the buffy coat can be lysed by adding a hypotonic ammonium chloride solution or other red cell lysing reagent to generate a purified buffy coat preparation.
9. This cell preparation would be processed for PCR or other analysis using standard methodologies.

Preferably, the buffy coat is collected within 24 hours from the time of donation.

Other methods can be used to obtain the buffy coat, such as the Baxter Opti-System.

Figure 3:
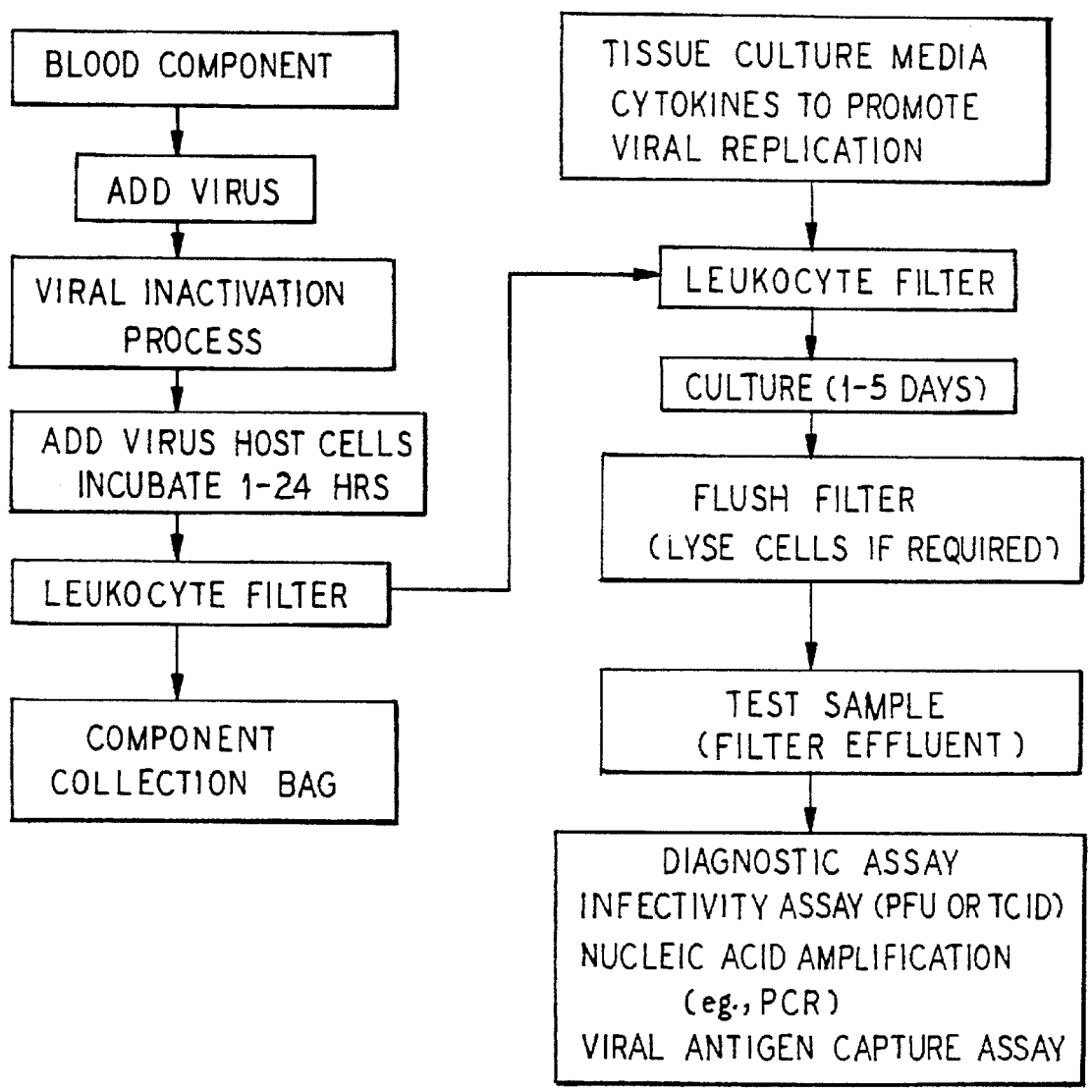
FIG. 3 illustrates schematically the use of an embodiment of the present invention for validating virus depletion/inactivation process.

FIG. 3 illustrates schematically another embodiment of the present invention that can be used for purposes of validating virus depletion/inactivation processes. The method consists of adding virus (e.g., HIV) to a blood component and then treating the blood with a viral inactivation/removal process. Of course, naturally infected blood can be used if desired.

Next, virus host cells are added to the blood (e.g., H9 cells for HIV or Vero cells for VSV). The cells are allowed to incubate in the whole volume of the blood component. During this incubation step, that will last from 1 to 18 hours, infectious virus present in the blood component attach to and penetrate the host cells to initiate the infection process.

In a further step, pursuant to the present invention, the virus host cells are harvested and separated from the blood cells by use of a leukocyte filter. The filter removes cell lines used for viral infectivity studies. Additionally, the filter will remove and separate the leukocytes from platelets and red cells.

The filter is then washed with tissue culture media, such as 10% Fetal Calf Serum in RPMI 1640 media, as required to support the viral host cells. The filter is then incubated at 37° C. for 6–120 hours to allow a virus to continue propagating in the host cells contained in the filter.

At the end of the incubation period, an effluent is prepared from the filter (with or without lysing the host cells) to be used as the test material. The effluent is prepared by flushing the filter with a lysis buffer such as 1% Triton X-100 (Sigma Chemical Co.); 10 mM Tris-HCL, pH 7.0; 1 mM EDTA or a hypotonic solution that lysis the leukocytes but does not inactivate the virus.

The test material is then either tested for infectious virus using conventional tissue culture infectivity assays (e.g., plaque-forming units) or for viral nucleic acid markers (e.g., HIV-DNA sequences using PCR) or viral antigens (e.g., HIV p24 antigen).

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for providing a blood component to a recipient comprising the steps of:

removing and collecting, using a centrifugation process, from a blood unit that includes at least a buffy coat layer containing leukocytes, a red blood cell rich layer and a platelet rich layer, the buffy coat layer without rendering the red blood cell rich layer and the platelet rich layer unusable for therapeutics;

using a nucleic acid sequencing technique to test the leukocytes that have been collected for the presence of viral nucleic acid sequences; and administering at least one of the red blood cell rich layers or the platelet rich layer to the recipient if the test demonstrates that the blood unit does not contain viral contamination.

2. A method for providing a blood component to a recipient using a procedure that includes testing a blood unit for viral contamination without rendering at least a platelet rich plasma layer and a red blood cell rich layer of the blood unit unusable for therapeutic applications comprising the steps of:

separating a whole blood unit into a platelet rich plasma layer, a red blood cell rich layer, and a buffy layer;

removing the buffy layer from the platelet rich plasma layer and red blood cell layer using a means that does not require filtering, and assaying the buffy layer for viral contamination; and if the assay determines no viral contamination is present in the buffy layer, using at least one of the platelet rich plasma layer or red blood cell rich layer for therapeutic applications.

3. The method of claim 2 wherein the buffy layer is assayed using nucleic acid amplification.

4. The method of claim 2 wherein the buffy layer is assayed using a viral antigen capture test.

5. The method of claim 2 wherein the blood unit is separated by centrifugation.

* * * * *